United States Patent
Anderson et al.

(10) Patent No.: US 9,855,166 B2
(45) Date of Patent: Jan. 2, 2018

(54) METHOD AND APPARATUS FOR CRYOGENIC TREATMENT OF SKIN TISSUE

(71) Applicant: The General Hospital Corporation, Boston, MA (US)

(72) Inventors: Richard Rox Anderson, Boston, MA (US); Dieter Manstein, Coral Gables, FL (US); Henry HL Chan, Boston, MA (US); Joseph Ting, Boston, MA (US)

(73) Assignee: THE GENERAL HOSPITAL CORPORATION, Boston, MA (US)

( * ) Notice: Subject to any disclaimer, the term of this patent is extended or adjusted under 35 U.S.C. 154(b) by 89 days.

(21) Appl. No.: 14/358,329

(22) PCT Filed: Nov. 16, 2012

(86) PCT No.: PCT/US2012/065664
§ 371 (c)(1),
(2) Date: May 15, 2014

(87) PCT Pub. No.: WO2013/075016
PCT Pub. Date: May 23, 2013

(65) Prior Publication Data
US 2014/0303696 A1    Oct. 9, 2014

Related U.S. Application Data

(60) Provisional application No. 61/560,632, filed on Nov. 16, 2011.

(51) Int. Cl.
*A61F 7/00* (2006.01)
*A61B 18/02* (2006.01)
(Continued)

(52) U.S. Cl.
CPC ............ *A61F 7/0085* (2013.01); *A61B 18/02* (2013.01); *A61F 7/007* (2013.01); *A61F 7/02* (2013.01);
(Continued)

(58) Field of Classification Search
CPC ................................................ A61F 2007/0087
See application file for complete search history.

(56) References Cited

U.S. PATENT DOCUMENTS 3,664,344 A    5/1972 Bryne
4,206,609 A    6/1980 Durenec
(Continued)

FOREIGN PATENT DOCUMENTS

CN    1741777 A    3/2006
CN    101669841    3/2010
(Continued)

OTHER PUBLICATIONS

Lewis, Thomas. "The Blood Vessels of the Human Skin". The British Medical Journal. Jul. 10, 1926. pp. 61-62.*
(Continued)

*Primary Examiner* — Long V Le
*Assistant Examiner* — Luther G Behringer
(74) *Attorney, Agent, or Firm* — Andrews Kurth Kenyon LLP (57) ABSTRACT

Cosmetic method and apparatus are provided that can provide cooling and/or freezing of skin tissue proximal to the skin surface to generate an appearance of lightening or reduced pigmentation in the skin. The skin can be cooled to a temperature of less than about −5 degrees Celsius for a duration of about one minute or less, using a cooled surface that is at least 3 cm in width. A cooling arrangement can be provided to provide controlled heat removal from the skin
(Continued)

tissue being treated. A sensor can optionally be provided to detect freezing of tissue proximal to the cooled surface.

22 Claims, 5 Drawing Sheets

(51) Int. Cl.
  *A61F 7/02* (2006.01)
  *A61B 17/00* (2006.01)
  *A61B 18/00* (2006.01)

(52) U.S. Cl.
  CPC .............. *A61B 2017/00057* (2013.01); *A61B 2018/0047* (2013.01); *A61B 2018/00452* (2013.01); *A61B 2018/00791* (2013.01); *A61B 2018/0237* (2013.01); *A61F 2007/0075* (2013.01); *A61F 2007/0095* (2013.01)

(56) References Cited

U.S. PATENT DOCUMENTS

| | | | |
|---|---|---|---|
| 4,614,191 | A * | 9/1986 | Perler .............................. 607/96 |
| 5,505,726 | A * | 4/1996 | Meserol ............................ 606/9 |
| 5,596,875 | A | 1/1997 | Berry et al. |
| 5,759,182 | A | 6/1998 | Varney et al. |
| 5,848,981 | A | 12/1998 | Herbranson |
| 6,017,337 | A | 1/2000 | Pira |
| 6,430,956 | B1 | 8/2002 | Haas et al. |
| 6,503,246 | B1 | 1/2003 | Har-Shai et al. |
| 6,629,417 | B2 | 10/2003 | Haas et al. |
| 6,981,970 | B2 | 1/2006 | Karni |
| 7,630,774 | B2 | 12/2009 | Karni et al. |
| 7,751,452 | B2 | 7/2010 | Vogler |
| 7,850,683 | B2 | 12/2010 | Elkins |
| 8,150,532 | B2 | 4/2012 | Karni et al. |
| 8,435,194 | B2 | 5/2013 | Dverin et al. |
| 8,579,835 | B2 | 11/2013 | Britva et al. |
| 8,758,419 | B1 * | 6/2014 | Quisenberry ......... A61F 7/0085 607/104 |
| 8,950,406 | B2 | 2/2015 | Karni |
| 2003/0100936 | A1 | 5/2003 | Altshuler et al. |
| 2004/0167592 | A1 * | 8/2004 | Grove .................. A61B 18/082 607/96 |
| 2005/0222565 | A1 | 10/2005 | Manstein et al. |
| 2005/0251120 | A1 | 11/2005 | Anderson |
| 2006/0189976 | A1 | 8/2006 | Karni et al. |
| 2007/0010861 | A1 | 1/2007 | Anderson |
| 2007/0088386 | A1 | 4/2007 | Babaev |
| 2007/0129714 | A1 | 6/2007 | Elkins |
| 2007/0135876 | A1 | 6/2007 | Weber |
| 2007/0185527 | A1 | 8/2007 | Babaev |
| 2008/0039747 | A1 | 2/2008 | Baerwalde et al. |
| 2008/0077211 | A1 | 3/2008 | Levinson |
| 2008/0119839 | A1 | 5/2008 | Vancalette |
| 2008/0183167 | A1 | 7/2008 | Britva et al. |
| 2008/0287943 | A1 | 11/2008 | Weber et al. |
| 2009/0012585 | A1 | 1/2009 | Karni et al. |
| 2009/0171424 | A1 | 7/2009 | Britva et al. |
| 2009/0281537 | A1 | 11/2009 | Britva et al. |
| 2010/0036295 | A1 | 2/2010 | Altshuler et al. |
| 2010/0081971 | A1 * | 4/2010 | Allison .............................. 601/2 |
| 2010/0114007 | A1 | 5/2010 | Fischer et al. |
| 2011/0313411 | A1 | 12/2011 | Anderson et al. |
| 2012/0041525 | A1 | 2/2012 | Karni et al. |
| 2012/0071794 | A1 | 3/2012 | Karni |
| 2012/0123319 | A1 | 5/2012 | Britva et al. |
| 2012/0330194 | A1 | 12/2012 | Britva et al. |
| 2014/0007895 | A1 | 1/2014 | Britva et al. |
| 2014/0135662 | A1 | 5/2014 | Britva et al. |
| 2015/0045857 | A1 | 2/2015 | Britva et al. |
| 2015/0080991 | A1 | 3/2015 | Britva et al. |

FOREIGN PATENT DOCUMENTS

| | | |
|---|---|---|
| CN | 102098982 A | 6/2011 |
| CN | 102143724 A | 8/2011 |
| DE | 9217897 | 11/1993 |
| EP | 1797847 | 6/2007 |
| EP | 2201917 | 6/2010 |
| EP | 2272455 | 1/2011 |
| GB | 2286660 | 8/1995 |
| GB | 2286660 A | 8/1995 |
| JP | 04-133822 | 12/1992 |
| JP | 10-052475 | 2/1998 |
| JP | 2009-240795 | 10/2009 |
| KR | 20-0431404 | 11/2006 |
| KR | 10-0802155 | 2/2008 |
| RU | 2074680 | 3/1997 |
| WO | WO 03/078596 | 9/2003 |
| WO | WO 03/078596 A2 | 9/2003 |
| WO | WO 2005/096979 | 10/2005 |
| WO | WO 2006/066226 A1 | 6/2006 |
| WO | WO2006066226 | 6/2006 |
| WO | WO 2006/127467 | 11/2006 |
| WO | WO 2007/064718 | 6/2007 |
| WO | WO2008055243 | 5/2008 |
| WO | WO 2008/091983 | 7/2008 |
| WO | WO2008083305 | 7/2008 |
| WO | WO 2009/146053 | 12/2009 |
| WO | WO 2010/017477 | 2/2010 |
| WO | WO 2010/017477 A2 | 2/2010 |
| WO | WO 2010/007619 A1 | 10/2010 |
| WO | WO2013075006 | 5/2013 |
| WO | WO2013075016 | 5/2013 |

OTHER PUBLICATIONS

U.S. Appl. No. 60/886,587, filed Jan. 25, 2007, Bryan Weber.
U.S. Appl. No. 61/041,593, filed Apr. 1, 2008, Dieter Manstein.
U.S. Appl. No. 61/174,004, filed Apr. 30, 2009, Karni.
Har-Shai Y. et al., "Effect of skin surface temperature on skin pigmentation during contact and intralesional cryosurgery of keloids," J. Eur Acad Dermatol Vener. 21(2): 2007.
Extended European Search Report for European Application No. 12850636 dated Oct. 1, 2015.
The first Chinese Office Action and First Search Report for Chinese Application No. 201280066420.9 dated Jul. 1, 2015.
Israeli Office Action for Israeli Patent Application No. 211109 dated Jun. 19, 2012.
European Search Report for European Application No. 09805610.4 dated Aug. 2, 2012.
Chinese Office Action for Chinese Patent Application No. 200980134959.1 dated Mar. 29, 2013.
International Search Report and Written Opinion for International Application No. PCT/US2009/053153 dated May 11, 2010.
Y. Har-shai et al. "Effect of Skin Temperature on Skin Pigmentation During Contact and Intralesional Cryosurgery of Keloids" JEADV 2007,21, pp. 191-198 (2006).
The Second Office Action for Chinese Patent Application No. 200980134959.1 dated Jul. 17, 2014.
International Search Report for International Patent Application No. PCT/US2012/065643 dated Mar. 14, 2013.
International Written Opinion for International Patent Application No. PCT/US2012/065643 dated Mar. 14, 2013.
International Search Report for International Patent Application No. PCT/US2012/065664 dated Mar. 14, 2013.
International Written Opinion for International Patent Application No. PCT/US2012/065664 dated Mar. 14, 2013.
Y. Har-shai et al. "Effect of Skin Temperature on Skin Pigmentation During Contact and Intralesional Cryosurgery of Keloids" JEADV 2007, 21, pp. 191-198.
The Chinese Office Action and Search Report for Chinese Application No. 201280066420.9 dated May 18, 2016.
First Office Action for Japanese Application No. 2014-542518 dated Aug. 1, 2016.
Decision of Rejection dated Jan. 23, 2017 for Japanese Patent Application No. 2014-542518.

(56) References Cited

OTHER PUBLICATIONS

Third Chinese Office Action dated Dec. 6, 2016 for Chinese Patent Application No. 201280066420.9.
The Third Chinese Office Action for Chinese Patent Application No. 201280066420.9 dated Dec. 6, 2016.

* cited by examiner

METHOD AND APPARATUS FOR CRYOGENIC TREATMENT OF SKIN TISSUE

CROSS-REFERENCE TO RELATED APPLICATION(S)

This application relates to and claims priority from U.S. Provisional Patent Application No. 61/560,632, filed on Nov. 16, 2011, the entire disclosure of which is incorporated herein by reference in its entirety.

FIELD OF THE DISCLOSURE

The present disclosure relates to a cosmetic method and apparatus for improving skin appearance. More specifically, the present disclosure is relates to exemplary embodiments of such method and apparatus adapted to cool and/or freeze skin tissue to affect pigmentation, e.g., to lighten the appearance of the skin.

BACKGROUND INFORMATION

Controlled freezing of biological tissue, such as skin tissue, can produce various effects. Certain tissue freezing procedures and devices, such as conventional cryoprobes, can cause severe freezing of tissue and generate cellular damage. It has been observed that moderate degrees of freezing can produce particular effects, such as affecting the expression of skin pigmentation.

There is a demand for cosmetic products that can lighten the appearance of skin or otherwise controllably affect skin pigmentation. For example, it may be desirable to lighten the overall complexion or color of a region of skin to alter the general appearance for cosmetic reasons. Also, lightening of particular hyperpigmented regions of skin, such as large freckles, 'café au lait' spots, melasma, or dark circles under the eyes that may result from excessive local amounts of pigment in the skin, may also be desirable for cosmetic reasons. Hyperpigmentation can result from a variety of factors such as UV exposure, aging, stress, trauma, inflammation, etc. Such factors can lead to an excess production of melanin, or melanogenesis, in the skin by melanocytes, which can lead to formation of hyperpigmented areas. Such hyperpigmented areas are typically located within the epidermis; however, they can also result from excess melanin deposited within the dermis. Many topical formulations are being marketed that claim to lighten age spots and reduce the effects of such hyperpigmentation. However, these cosmetic formulations may have questionable effectiveness.

Hypopigmentation of skin tissue has been observed as a side effect in response to temporary cooling or freezing of the tissue, such as may occur during cryosurgery procedures. Loss of pigmentation following skin cooling or freezing may result from decreased melanosomes production, destruction of melanocytes, or inhibited transfer of melanosome into the keratinocytes in the lower region of the epidermal layer. The resultant hypopigmentation may be long-lasting or permanent. It has also been observed that some of these freezing procedures can generate regions of hyperpigmentation of skin tissue.

Accordingly, there may be a need to provide exemplary methods and apparatus that can provide controlled freezing of skin or other tissue, and gradual lightening of skin tissue that can address and/or overcome at least some of the deficiencies or issues described herein above.

SUMMARY OF EXEMPLARY EMBODIMENTS

The herein described embodiments pertain to a cosmetic method and apparatus. Synergetic effects may arise from different combinations of the features and embodiments described herein, although all such combinations might not be described in detail. Further, it shall be noted that all embodiments of the present disclosure concerning a method, might be carried out with the order of the steps as described, nevertheless this has not to be the only and essential order of the steps of the method. All different orders and combinations of the method steps are herewith described.

Exemplary embodiments of the present disclosure relate to non-invasive methods and apparatus for controlled cooling and freezing of skin tissue, which can reduce an overall pigmentation of an area of skin using cryogenic techniques. In one exemplary embodiment of the present disclosure, an apparatus can be provided for cooling or freezing large continuous regions of skin to produce a lightening of the skin appearance.

According to an exemplary embodiment of the present disclosure, the apparatus can include a cooling plate, preferably formed at least partially of a material having a large thermal effusivity, e.g., an effusivity at least 10 times greater than that of skin tissue. For example, the plate can be made at least partially of a metal or alloy, such as brass, gold, silver, copper, aluminum, or the like, diamond or diamond-like carbon, a frozen material, or another material that has a high thermal effusivity. The bottom surface of the plate can be configured to contact the surface of a region of skin, with a diameter or width that is greater than about 3 cm, or greater than about 5 cm, to facilitate uniform treatment of large areas of skin. The width of the plate along the bottom or skin contact surface can be, e.g., less than about 20 cm, 15 cm, 10 cm, 8 cm, or 5 cm. Such dimension can be large enough to treat large areas of skin in a reasonable time, while being small enough to facilitate accurate temperature and process control and/or to better conform to the shape of the skin surface. An insulated handle or cover can be provided for the apparatus to facilitate handling and positioning of the apparatus. The exemplary apparatus can be placed in a freezer such that the plate is cooled to subzero temperatures, and then positioned such that the bottom surface of the plate contact an area of skin to be treated.

In further exemplary embodiments of the present disclosure, a cooling arrangement can be provided in the apparatus. The cooling arrangement can include, e.g., a reservoir provided in thermal contact with the cooling plate. In certain exemplary embodiments, one or more such reservoirs can be formed within the cooling plate. A refrigerant or other heat-absorbing medium, such as a saline solution, a water-alcohol mixture, a water-glycol mixture, or the like can be provided in the reservoir to cool the plate. Optionally, a cooled refrigerant can be circulated through the reservoir and/or one or more ducts formed in the reservoir to provide continuous cooling to the plate. The cooling arrangement can be configured to control and/or maintain a particular temperature of the cooling plate while the cooling plate is in contact with the skin.

In another exemplary embodiment of the present disclosure, a Peltier device or other cooling device or source can be provided in thermal contact with the plate to cool it. In certain embodiments, a cooling plate may be omitted, and the bottom surface of the cooling device can be configured to be placed directly on the skin surface.

In a further exemplary embodiment of the present disclosure, a cosmetic method can be provided to produce hypopigmentation in skin tissue. In one exemplary embodiment, the method for lightening the appearance of skin can be provided that includes cooling and/or freezing a region of skin to induce localized hypopigmentation effects. Further lightening can be achieved by treating a particular region of skin more than once.

In a still further exemplary embodiment of the present disclosure, the cosmetic method can include freezing regions of skin tissue, for example, to at least the depth of the basal layer, e.g., to at least about the depth of the dermal-epidermal junction, which can provide a hypopigmentation effect. This freezing can preferably be achieved by contacting the skin surface with a cold object, e.g., a cooling plate or a portion of a cooling system or apparatus, that is provided at a temperature of about −5 degrees Celsius or colder, e.g., between about −7 and −10 degrees Celsius. In certain embodiments, temperatures as low as about −15 to −20 degrees Celsius can be used. Cooling or treatment times, which can correspond to the duration that the cold object is contacted with the skin surface after local tissue freezing begins, can be less than about two minutes, or preferably less than about one minute, e.g., between about 30 seconds and 1 minute when the temperature of the cold object is between about −7 and −10 degrees Celsius. Shorter cooling times can be used when the cold object is provided at colder temperatures, e.g. less than about 30 seconds or even less than about 15 seconds when the temperature of the cold object is between about −15 to −20 degrees Celsius. Such temperatures and times can lead to hypopigmentation responses in skin tissue while being fast enough to facilitate sequential cooling of a plurality of regions of skin. The above indicated features regarding minimum dimensions, maximum dimensions, and cooling times and temperatures can be arbitrarily combined by a skilled practitioner without departing from the disclosure of the present disclosure.

For example, one or more temperature and/or optical sensors, or other types of sensors, can be provided to control temperature of the cooling plate or device, to detect the local temperature of contacted/cooled tissue, and/or to detect local freezing of skin tissue while the cooling plate or device is placed in contact with the skin surface. Treatment time can be determined relative to the initiation of freezing, e.g., as a duration of contact time between the cold object and the skin surface after local tissue freezing has begun. Temperature can be measured using contact sensors, non-contacting sensors, or both. A heating arrangement can optionally be provided to warm the frozen tissue after the particular treatment time has elapsed. A feedback signal may be generated and sent to the cooling device such that undesired or excessive cooling is avoided. In other words, a feedback control can be provided to ensure a safe treatment procedure for which no danger or risk results for the person undergoing the treatment.

According to further exemplary embodiments of the present disclosure, method and apparatus for detection of tissue freezing at the onset of such freezing is provided. Such freezing detection, which can include temperature control and/or feedback, optical detection, and/or measurement of electrical and/or mechanical impedance of the skin tissue, will be described in more detail hereinafter.

This exemplary method can provide gradual lightening of the skin area being treated by forming depigmented areas. Multiple treatments can be used to lighten the area further. The exemplary methods and apparatus described herein may also improve the general appearance of the skin by stimulating a response in the small regions of frozen tissue.

It shall further be noted that the herein described cosmetic method has been tested, and is a safe and routine procedure that can be practiced in beauty parlors or other settings. The exemplary method can be a non-invasive a method. Moreover, the exemplary method can be safe as it is non-invasive, does not present a substantial health risk, and does not require professional medical expertise to be performed. No clinician is needed to perform the embodiments of the exemplary method described herein, and no risk, much less a health risk, is presented for a person being treated with said cosmetic method, as will become clear from the following description.

These and other objects, features and advantages of the present disclosure will become apparent upon reading the following detailed description of embodiments of the invention, when taken in conjunction with the appended claims.

BRIEF DESCRIPTION OF THE DRAWINGS

Further objects, features and advantages of the present disclosure will become apparent from the following detailed description taken in conjunction with the accompanying figures showing illustrative embodiments, results and/or features of the exemplary embodiments of the present disclosure, in which.

Throughout the drawings, the same reference numerals and characters, unless otherwise stated, are used to denote like features, elements, components, or portions of the illustrated embodiments. Similar features may thus be described by the same reference numerals, which indicate to the skilled reader that exchanges of features between different embodiments can be done unless otherwise explicitly stated. Moreover, while the present disclosure will now be described in detail with reference to the figures, it is done so in connection with the illustrative embodiments and is not limited by the particular embodiments illustrated in the figures. It is intended that changes and modifications can be made to the described embodiments without departing from the true scope and spirit of the present disclosure as defined by the appended claims.

DETAILED DESCRIPTION OF EXEMPLARY EMBODIMENTS

According to an exemplary embodiment of the present disclosure, a cryotherapy-based approach can be used to controllably and non-invasively freeze regions of skin tissue. Such freezing can lighten the overall appearance of the skin, or reduce the overall darkness of certain skin areas that have excess pigmentation. Contacting regions of skin with cold objects can inhibit formation and/or expression of pigment in the underlying skin. This effect can provide long-lasting or permanent lightening of the areas being treated.

Figure 1:
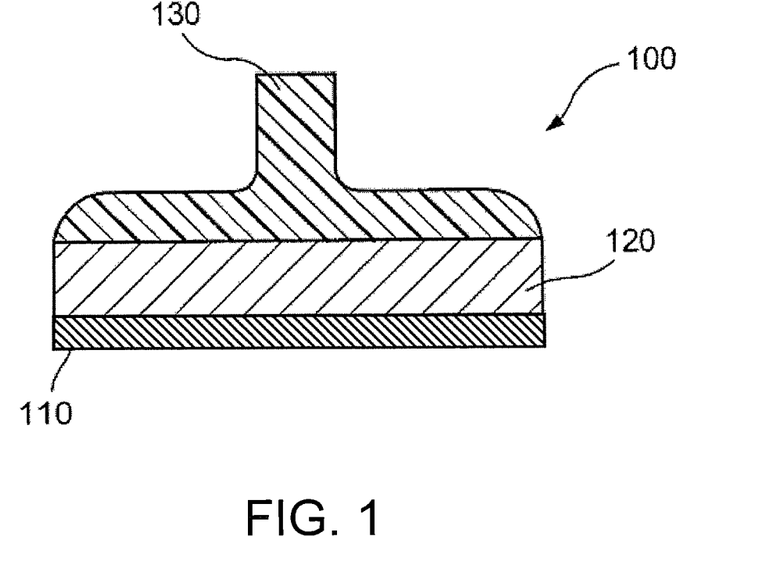
FIG. 1 is a side view of a first exemplary apparatus that can be used to produce a hypopigmentation cryogenically in a skin tissue according to an exemplary embodiment of the present disclosure.

FIG. 1 depicts an exemplary apparatus 100 for controllably freezing skin, e.g., to produce hypopigmentation in skin tissue, in accordance with exemplary embodiments of the present disclosure. The exemplary apparatus 100 can include a contact plate 110 attached to a cooling arrangement 120. The plate 110 can be provided in a thermal communication with the cooling arrangement 120. In certain exemplary embodiments, the plate 110 and the cooling arrangement 120 can be formed at least in part from a single material. An optional handle 130, which can be formed of an insulating material such as plastic, can be affixed to the cooling arrangement 120 to facilitate handling and positioning of the apparatus 100. The apparatus 100 shown in FIG. 1 is not necessarily drawn to scale. For example, the general dimensions of the cooling arrangement 120 and the plate 110 are not limited to the proportions illustrated in the FIG. 1. In one exemplary embodiment, the cooling arrangement 120 can be provided as a substrate that is relatively thick from top to bottom as compared to the lateral dimensions, and it may be much thicker than the plate 110 in certain embodiments.

The plate 110 can be formed from a metal or a metal alloy, or another material having a high thermal effusivity, e.g., such that values of these thermophysical properties are greater than the corresponding values for skin tissue. For example, the plate 110 can be made of brass, copper, silver, aluminum, graphite, diamond, diamondlike carbon, other materials which are used in conventional contact cryoprobes, or combinations thereof. The cooling arrangement 120 can be formed from the same material or another material having similar thermophysical properties. For example, the plate 110 can be formed from materials having a much higher thermal conductivity than the skin tissue, and can be used to facilitate an extraction of heat from the portion of the tissue contacted by the cooling plate 110. Further, materials having a much higher thermal effusivity than the skin tissue, e.g. at least 10 times the thermal effusivity of skin, can be held at a cold temperature, and extract heat from the portion of tissue contacted by the cooling plate 110.

The bottom surface of the plate 110 can be substantially flat and/or slightly rounded to provide good thermal contact with skin tissue when the apparatus 100 is placed on the area of the skin to be treated. The plate 110 can have a large width or diameter configured to contact the surface of a region of skin, e.g., a diameter or width that is greater than about 3 cm, or greater than about 5 cm, to facilitate treatment of large areas of skin. A maximum dimension of the surface of the plate 110 configured to contact the skin surface can be, for example, about 20 cm, 15 cm, 10 cm, 8 cm, 5 cm or 3 cm, e.g., between about 3 cm and 20 cm. Such dimension can provide rapid treatment of larger areas of skin while facilitating accurate temperature and process control and/or better conforming to the shape of the skin surface.

The plate 110 can be formed of a metal such as copper, silver, or aluminum. A layer or coating of another material having a still higher thermal effusivity than the material of the plate 110, can be optionally provided on the bottom surface of the plate 110. For example, diamond and diamond like carbon have very high thermal effusivities, and a layer of one of these materials on the bottom surface of the plate 110 can improve thermal transfer between the cooling plate 110 and the skin being treated.

A cold environment can be provided to cool the apparatus 100 to a particular temperature. For example, the exemplary apparatus 100 can be placed in a freezer to cool the plate 110 and the cooling arrangement 120 to a particular temperature. Alternatively, the plate 110 and/or the cooling arrangement 120 can be cooled by spraying with a refrigerant such as liquid nitrogen, or immersion in a cold bath, such a chilled solution of alcohol and water or a cold saline solution. Preferably, the bath can be maintained at a predetermined temperature. After cooling, the bottom surface of the plate 110 can then be pressed against an area of skin to be lightened for a predetermined time, which can locally chill and/or freeze a portion of skin tissue. For example, the plate 110 and the cooling arrangement 120 can preferably be cooled to at least −5 degrees Celsius or colder, e.g., between −5 or −7 degrees and −10 degrees Celsius, or even as cold as −15 to −20 degrees Celsius, so that the plate 110 can cool skin tissue sufficiently and freeze at least a portion of the skin tissue when the apparatus 100 is brought into contact with the skin surface, which can also produce a hypopigmentation response.

In a further exemplary embodiment, a skin freezing system can be provided that includes the apparatus 100 and the above-described cold environment, such as a refrigerated enclosure, a cold bath containing a chilled solution or a slush, a conduit circulating cold liquid or gas, or the like. The cold environment can be configured to cool or pre-cool the apparatus 100 to a particular temperature. In further embodiments, a system can be provided that includes such a cold environment and any of the exemplary apparatuses described herein, where the cold environment can be configured to cool or pre-cool at least a portion of such apparatus.

Figure 2:
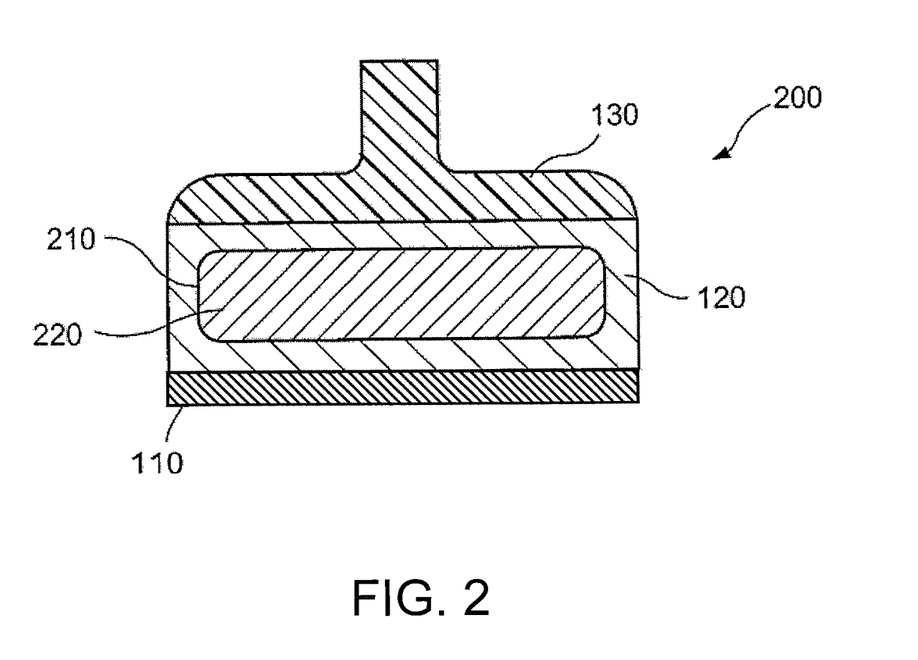
FIG. 2 is a side cross-sectional view of a second exemplary apparatus that can be used to produce the hypopigmentation cryogenically in the skin tissue according to an exemplary embodiment of the present disclosure.

In a further exemplary embodiment shown in FIG. 2, an apparatus 200 can be provided, where the cooling arrangement 120 of the apparatus 200 can include a hollow reservoir 210 that contains a refrigerant 220. The refrigerant 220 can be a material that freezes, for example, at a temperature below 0 degrees Celsius. Such a refrigerant 220, when frozen in the reservoir 210, can facilitate cooling of the cooling arrangement 120 and/or the plate 110 at colder temperatures for an extended period of time.

In certain exemplary embodiments of the present disclosure, the refrigerant 220 can be selected such that it exhibits a solid-liquid phase change at a particular temperature or a temperature range, for example, at least as cold as about −5 degrees Celsius, e.g., about −7 to −10 degrees Celsius, or optionally as cold as about −15 to −20 degrees Celsius. For example, when the exemplary apparatus 200 warms up to the phase change temperature or temperature range (if it is initially colder), the refrigerant 220 can maintain the temperature of the cooling arrangement 120 and/or the plate 110 at approximately the phase change temperature or within a particular phase change temperature range for an extended period of time (e.g., during longer contact periods between the plate 110 and the skin tissue being treated, or during application of the apparatus 200 to a plurality of regions of skin being treated). Heat extracted from the skin tissue can be conducted through the plate 110 and the cooling arrangement 120 to the refrigerant 220, which can absorb the heat at a relatively constant temperature as the phase change in the refrigerant 220 progresses. This exemplary arrangement can facilitate a predictable and repeatable rate of heat transfer flow from the skin contacting the plate 110 because the temperature difference provided by the apparatus 200 can be maintained substantially constant. This exemplary embodiment can also provide cooling and/or freezing of the upper portion of the skin tissue at a particular temperature or within a narrow range of temperatures, e.g., between about −5 or −7 degrees and −10 degrees Celsius.

A thermal conduction between the skin tissue and the cooling arrangement 120 can be improved if the plate 110 is relatively thin, e.g., on the order of a few millimeters. Such a thin plate 110 can facilitate maintenance of the surface skin temperature closer to the cold temperature of the cooling arrangement 120 when the apparatus 200 is placed in contact with the skin surface. In the various embodiments described herein, the plate 110 (if present) is preferably configured to provide a good thermal communication between the skin surface and the cooling arrangement 120.

Figures 3A, 3B:
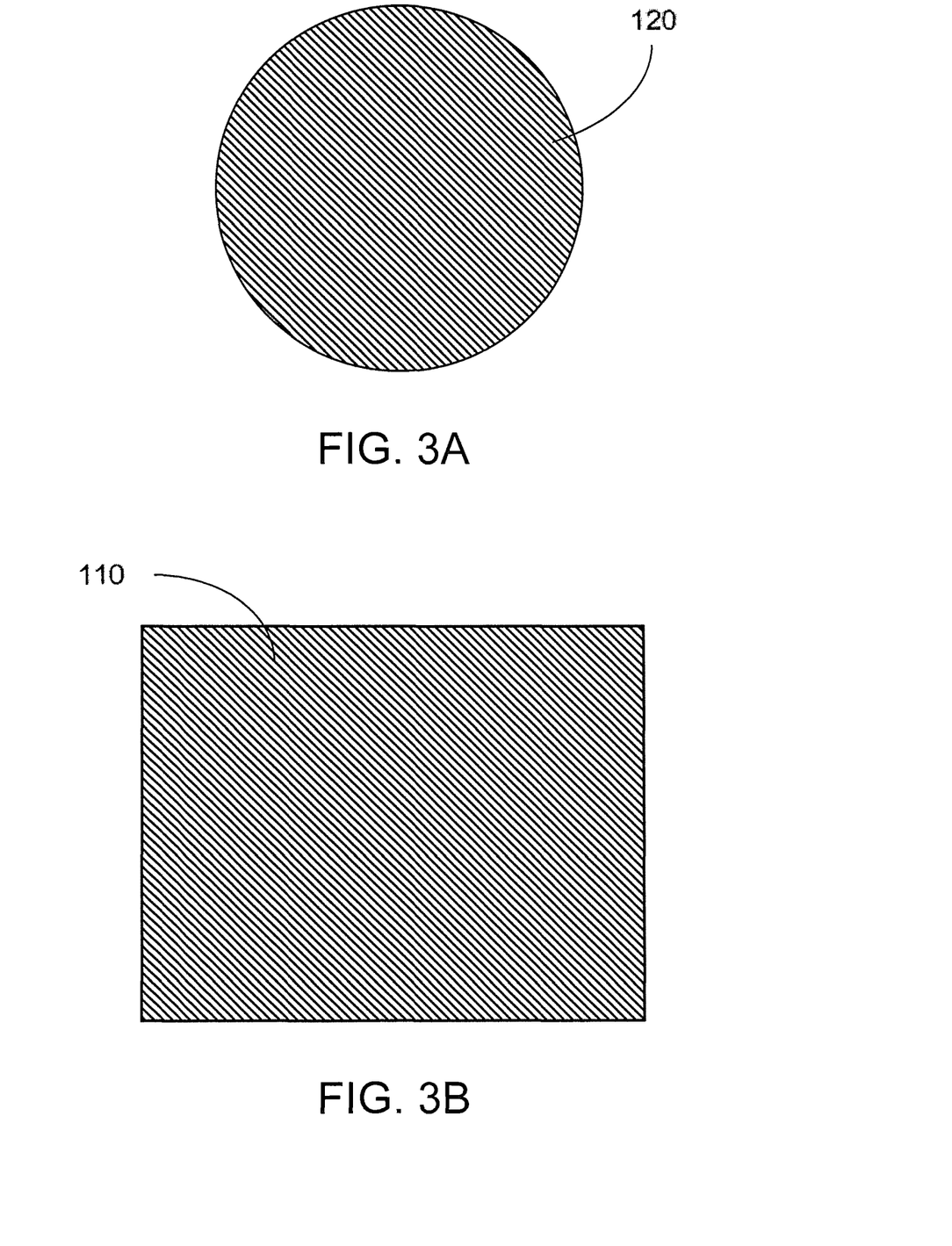
FIG. 3A is a bottom view of a first exemplary configuration of cooling plate that can be used to produce the hypopigmentation in the skin tissue according to an exemplary embodiment of the present disclosure.
FIG. 3B is a bottom view of a second exemplary configuration of the cooling plate that can be used to produce the hypopigmentation in the skin tissue according to an exemplary embodiment of the present disclosure.
Figure 3C:
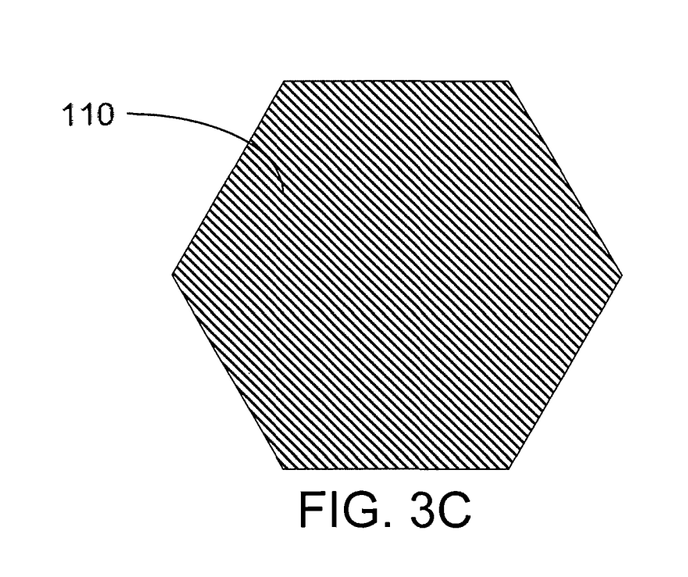
FIG. 3C is a bottom view of a third exemplary configuration of the cooling plate that can be used to produce the hypopigmentation in the skin tissue according to an exemplary embodiment of the present disclosure.

A bottom view of an exemplary plate 110 provided in thermal communication with the cooling arrangement 120 is shown in FIG. 3A. The plate 110 in this embodiment can be provided with an approximately circular shape. In a further exemplary embodiment, illustrated in FIG. 3B, the plate 110 provided on the bottom of the cooling arrangement 120 can be provided with a substantially square or rectangular shape. The aspect ratio of this exemplary shape can be varied in different embodiments. For example, the plate 110 can be substantially square, as shown in FIG. 3B, or it may be a rectangle that is longer than it is wide. In a still further embodiment, shown in FIG. 3C, the plate 110 can be provided with a substantially hexagonal shape. A square, rectangular or hexagonal shape for the plate 110, as shown in FIGS. 3B and 3C, can facilitate uniform coverage of a larger area of skin tissue by sequential placement of the apparatus 200 on adjacent regions of skin tissue, such that substantially all of the desired treatment area of skin has been cooled by the apparatus 200 with little or no overlap of such treatment regions. Other plate shapes can also be provided, e.g., to conform to particular regions of skin and provide better contact and more effective cooling. The lower surface of the plate 110 can be planar, or it may be curved or contoured (e.g., convex or concave) to also better conform to the contours of the skin area being cooled.

The exemplary apparatus 100, 200 can facilitate substantially uniform treatment of a larger area of skin. For example, the apparatus 100, 200 may be sequentially applied to a plurality of adjacent regions of skin to treat areas larger than the size of the contact surface. Edge conduction effects near the perimeter of the plate 110 can lead to a slightly lesser degree of cooling or heat extraction in regions of skin tissue adjacent to the plate perimeter. Such effects can help to avoid excessive cooling in such regions if successive placements of the apparatus 100, 200 on the skin overlap somewhat in these regions.

The size of the cooling arrangement 120 and plate 110 can also be selected in part based on the size of the area being treated. For example, depigmentation of small areas can be achieved using a relatively small cooling arrangement 120 and plate 110, e.g., on the order of 3-5 centimeters in width. A larger plate 110 (and correspondingly larger cooling arrangement 120) can be provided to treat larger areas of the skin with a single application, and reduce the overall treatment time for larger areas of skin that require multiple placements of the apparatus 100, 200 against adjacent skin treatment areas.

The different exemplary geometrical characteristics of the sizes and shapes associated with the plate 110, described above with respect to FIGS. 3A-3C, can be used with any of the various embodiments described herein.

The exemplary apparatus 100 or the exemplary apparatus 200 can be cooled, for example, by placing the entire apparatus in a freezer and/or by exposing it to another cold material or environment. The plate 110 can be cooled to a temperature at which it can induce contact freezing in skin tissue. The cooling arrangement 120 can also cooled to the same temperature. The cooled cooling arrangement 120 can provide a thermal sink or reservoir that can help maintain the plate 110 at or close to the cooled temperature while portions of the apparatus 100 (e.g., the lower surface of the plate 110) are in contact with skin tissue.

Figure 4:
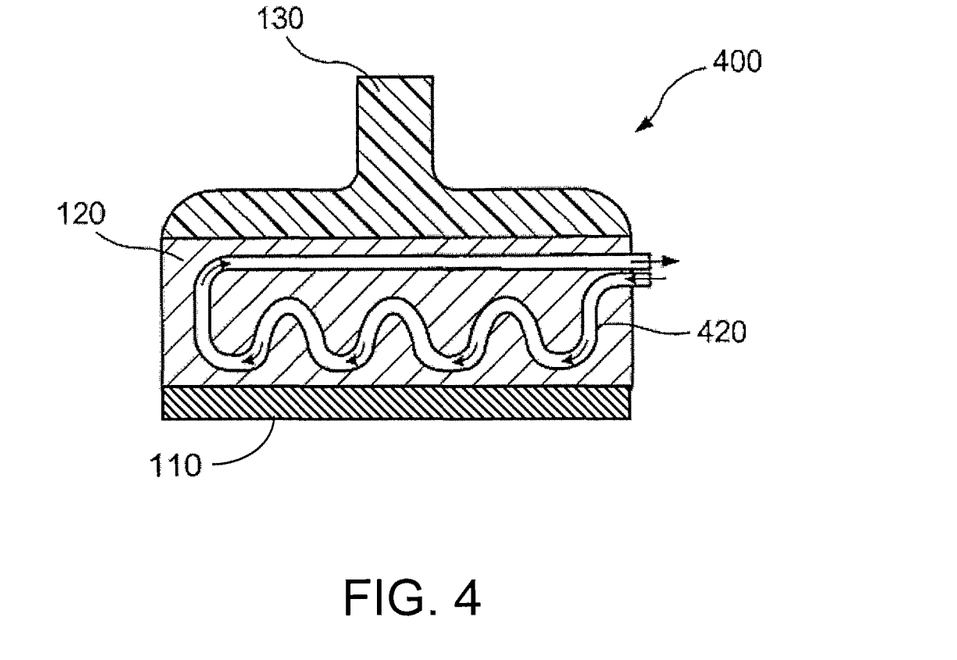
FIG. 4 is a side cross-sectional view of a third exemplary apparatus that can be used to produce the hypopigmentation cryogenically in the skin tissue according to an exemplary embodiment of the present disclosure.

In a further exemplary embodiment of the present disclosure, an exemplary apparatus 400 can be provided as shown in FIG. 4A. The cooling arrangement 120 of the exemplary apparatus 400 can include one or more conduits or channels 420 therethrough. A cooled refrigerant or cooling medium can be circulated through the channels to cool the cooling arrangement 120 and the plate 110, and optionally to maintain them at a particular temperature. The refrigerant can be any refrigerant described herein above, e.g., a saline solution, a water-alcohol mixture, a water-glycol mixture, a slush or phase-change material, etc. For example, a conventional fluid pump (not shown) can be used to circulate the refrigerant or cooling medium through the channels 420 in the cooling arrangement 120. Such pump can be located remotely from the apparatus 400, or in certain embodiments it can be affixed to the apparatus 400. The refrigerant can also be provided in a reservoir (not shown) that can be insulated and/or actively cooled using conventional techniques. The apparatus can further include a thermal control arrangement configured to maintain a particular temperature of the refrigerant, e.g., using one or more temperature sensors provided in communication with an active cooling arrangement as described herein. The refrigerant reservoir can be located remotely from the apparatus 400. Alternatively, the reservoir can be affixed thereto or formed as part of the apparatus 400 in further embodiments.

Figure 5:
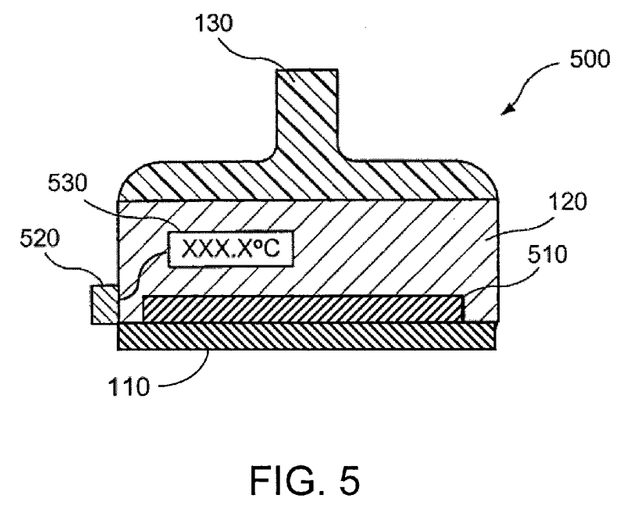
FIG. 5 is a side cross-sectional view of a fourth exemplary apparatus that can be used to produce the hypopigmentation cryogenically in the skin tissue according to an exemplary embodiment of the present disclosure.

In a still further exemplary embodiment of the present disclosure, an exemplary apparatus 500 can be provided, as shown in FIG. 5. The cooling arrangement 120 can include one or more Peltier devices 510 configured to cool a portion of the apparatus 500, e.g., to a particular temperature. The cold side of the Peltier device 510 can be provided in thermal contact with the plate 110. In a further exemplary embodiment, the plate 110 (or a portion thereof) can be omitted, such that the cold side of the Peltier device 510 is configured to contact the skin surface directly. A power source for powering the Peltier device 510 can be provided as part of the apparatus 500, or alternatively an external power source can be provided separate therefrom. The upper or warm side of the Peltier device 510 can be cooled by contacting it with a cooled object, by allowing or directing air or another gas to flow over at least a portion of it, and/or by other conventional cooling or ventilation techniques.

A temperature sensor 520 can be provided proximal to the lower portion of the cooling arrangement 120 or the plate 110. The temperature sensor can include, e.g., one or more thermocouples or thermistors or the like. Such temperature sensor 510 can be connected to a display 530 to indicate the temperature of the apparatus 500 near the plate 110. The display 530 can be provided on the apparatus 500, as shown in FIG. 5, or remote from the apparatus 500. The temperature sensor 520 can also be connected to the Peltier device 510 or any other active cooling arrangement as part of a control system to maintain the cooling arrangement 120 and/or plate 110 at or near a predetermined temperature. In other words, a feedback control can be provided based on the sensor 520 to ensure that no danger results for the person undergoing the treatment. Thus, a feedback signal may be generated and sent to the cooling device such that undesired or excessive cooling is avoided. This may provide for a highly safe treatment. Wire-based communication and/or wireless communication may be provided between components of the apparatus of the present disclosure. This will be explained in more detail below with regards to the figures. Such sensors and temperature control can be used in combination with any of the embodiments described herein.

Figure 6:
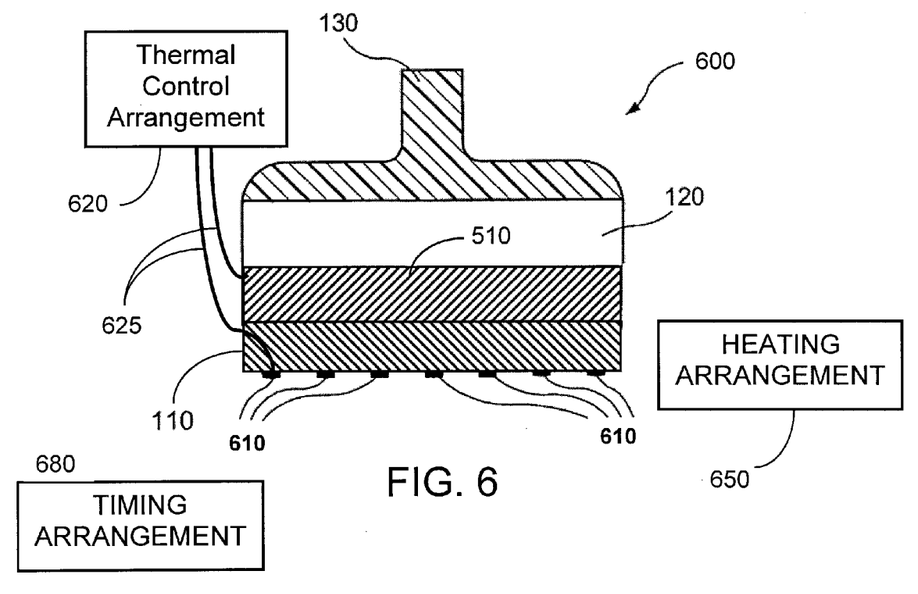
FIG. 6 is a side cross-sectional view of a fifth exemplary apparatus that can be used to produce the hypopigmentation cryogenically in the skin tissue according to an exemplary embodiment of the present disclosure.

In yet another exemplary embodiment, an exemplary apparatus 600 shown in FIG. 6 can be provided that includes a cooling arrangement 120, an optional handle 130, and an optional cooling plate 110. The cooling arrangement 120 can include, e.g., a Peltier device 510, a controlled-temperature reservoir 210 or channels 420 circulating a refrigerant (not shown), or the like, that can be provided in thermal communication with the plate 110 similar to the apparatus 200, 400, 500 shown in FIGS. 2, 4 and 5, respectively. One or more temperature sensors 610 can be provided on or near the lower surface of the plate 110, or on or near the bottom surface of the cooling arrangement 120 (e.g., the cold side of the Peltier device 510) if a cooling plate 110 is not provided. For example, the temperature sensor 610 can include a thermistor, a thermocouple, a resistance temperature detector (RTD), or the like. The temperature sensor 610 can cover a small portion of this bottom surface, which can reduce the effect of the mass and material of the sensor on local heat transfer between the bottom surface and the skin surface. Alternatively, the sensor 610 can be configured to cover substantially the entire bottom surface (e.g., it can be provided as a thin-film sensor), which can provide a more stable and/or accurate signal, and can also have a predictable effect on the local heat transfer. In certain embodiments, the temperature sensor 610 can be embedded in or provided with a material having a high thermal conductivity that covers a large portion or substantially all of the bottom surface. In these exemplary configurations, the sensors 610 may detect a composite temperature that depends on both the local temperature of the bottom surface of the plate 110 and the skin surface temperature when the apparatus 600 is placed on the skin.

Wires 625 or other communication arrangements can be provided between the temperature sensors 610 and a thermal control arrangement 620, and between the thermal control arrangement 620 and the cooling arrangement 120 (e.g., Peltier device 510, temperature controller associated with reservoir 210, or temperature control and/or pump used to cool and circulate refrigerant in channels 420). The wires 625 can be passed through a portion of the cooling plate 110, or optionally can be routed from the side of the plate 110 and along the bottom surface thereof, or both. The thermal control arrangement 620 can be provided external to the apparatus 600, or it can be mounted on or within the apparatus 600, and can optionally be integrated with the cooling arrangement 120. Optionally, a wireless communication between the sensor 610 and the thermal control arrangement 620 can be provided within this embodiment. Consequently, the thermal control arrangement 620 in combination with the sensor or sensors 610 can provide for a temperature feedback control based on temperatures detected at the cooling plate 110. This may increase the safety and/or reliability of the apparatus and the corresponding method.

The thermal control arrangement 620 can be configured to control characteristics of the operation of the Peltier device 510, e.g., based on signals received from the one or more temperature sensors 610. For example, the thermal control arrangement 620 can be configured to detect signals from the temperature sensors 610 and to vary the power characteristics provided to the Peltier device 510 (e.g., turn power on/off, reduce/increase power, and/or alter the duty cycle characteristics of the power) based on these signals. The thermal control arrangement 620 can be configured to use a proportional, integral, and/or derivative feedback algorithm to control the operation of the Peltier device 510, e.g., to maintain the bottom surface of the plate 110 or Peltier device 510 at a predetermined temperature or to approximate a predetermined temperature profile over time. Such control algorithms are known in the art. The thermal control arrangement 620 and sensors 610, as described above, can also be provided and used with the other cooling arrangements 120 as described herein, e.g., by controlling temperature of the reservoir 210 (if present) or controlling refrigerant temperature and/or circulation rate through channels 420 (if present), or by controlling temperature of still other types of cooling arrangements known in the art.

Further, thermal control arrangement 620 can be configured to control the Peltier device 510 or other cooling arrangement 120 based on a received temperature signal and to modify or affect at least one parameter chosen from the group comprising cooling temperature, cooling time, cooling duration, and any combination thereof.

It has been observed that cooling the basal layer of the skin (e.g., proximal to the dermal-epidermal junction) by cooling a surface of the skin to a particular temperature for a particular treatment time (which can be determined as a time interval that begins when local freezing of tissue begins) can produce hypopigmentation effects. Accordingly, any of the apparatuses described herein can be configured to provide one or more surfaces (e.g. the cooling plate 110, 610) at a temperature of about −5 degrees Celsius or colder, e.g., between about −5 degrees and −10 degrees Celsius, or preferably between about −7 to −10 degrees Celsius. Treatment times corresponding to these temperatures can be, e.g., less than about one minute, for example, about 45 seconds to one minute, or even as short as about 30 seconds in some embodiments. Such combinations of temperatures and times that generate freezing in tissue can produce hypopigmentation effects in skin without producing depigmentation (i.e., total pigmentation loss).

In further exemplary embodiments, the temperature of the cooling plate 110, 610 can be colder than −10 degrees Celsius, e.g., as cold as −15 or −20 degrees Celsius, with correspondingly shorter contact or treatment times, to generate sufficient local cooling and freezing of the tissue without inducing undesirable tissue damage from excessive cooling. For example, treatment times can be as short as 15 seconds or less, e.g., about 5 seconds, at these temperatures of between about −15 and −20 degrees Celsius. Such colder temperatures can be used, for example, to facilitate faster treatment times, and/or to compensate for such effects as thermal inefficiencies in the heat conduction through the cooling plate 110, 610 and/or warming effects of the skin that may be heated by local blood flow. In any of the embodiments described herein, the temperature, sensor and/or control parameters, placements and arrangements can be associated with the bottom surface of the cooling arrangement 120 (e.g., the cold side of the Peltier device 510) if no cooling plate 110 is provided.

Any of the exemplary apparatuses described herein can be further configured to maintain the temperature of the cooling plate 110, 610 at a substantially constant temperature when the cooling plate is contacted with the skin surface. The substantially constant temperature can include any of the temperatures described above. Maintaining the temperature can be achieved by, e.g., using an active cooling system, providing appropriate sensors, control arrangements, and/or a control feedback system as described herein, and/or providing a cooling arrangement and/or cooling plate 110, 610 that has a sufficiently large thermal effusivity and/or thermal mass to maintain the temperature substantially constant while the apparatus is placed in contact with the skin surface, using a phase-change material in a reservoir 210, etc.

The temperature can preferably be low enough to locally freeze at least a portion of the epidermal layer of the skin tissue proximal to the bottom surface of the cooling plate 110, 610 when this surface is brought into contact with the area of the skin to be treated. The bottom surface of the plate 110, 610 can be placed in contact with the region of the skin being treated for a duration of time sufficient to generate subsequent hypopigmentation of the frozen regions. This exemplary time duration can be determined as a time interval following initiation of local freezing of the skin tissue. Inducing local freezing of the upper layers of skin tissue (e.g., down to the basal layer) at these temperatures can also improve the hypopigmentation response. Portions of the upper dermal layer can also be frozen. This time duration can be greater than about 15 seconds. The treatment time is preferably not so long as to cause excessive freezing and issue damage in the cooled or frozen tissue. For example, if the bottom surface of the plate 110, 610 are maintained at a temperature of between about −5 and −10 degrees Celsius, a contact time between about 30 and 60 seconds may be sufficient to induce local freezing of the skin surface region that can lead to hypopigmentation. In general, an appropriate time of contact can be determined based on the geometry, materials, and initial cooled temperature of the exemplary embodiments of the apparatus described herein. The time and temperature used can be selected to produce a zone of frozen tissue proximal to the plate 110, 610 for a particular duration.

In certain exemplary embodiments, the material of the plate 110, 610 can be selected such that the corresponding apparatus is initially cooled, and the plate 110, 610 gradually warm up during prolonged contact with skin tissue. Accordingly, the plate 110, 610 can be provided in contact with the skin for longer periods of time, and gradual warming of the plate 110, 610 can prevent excessive freezing of the regions of skin proximal thereto.

Figure 7:
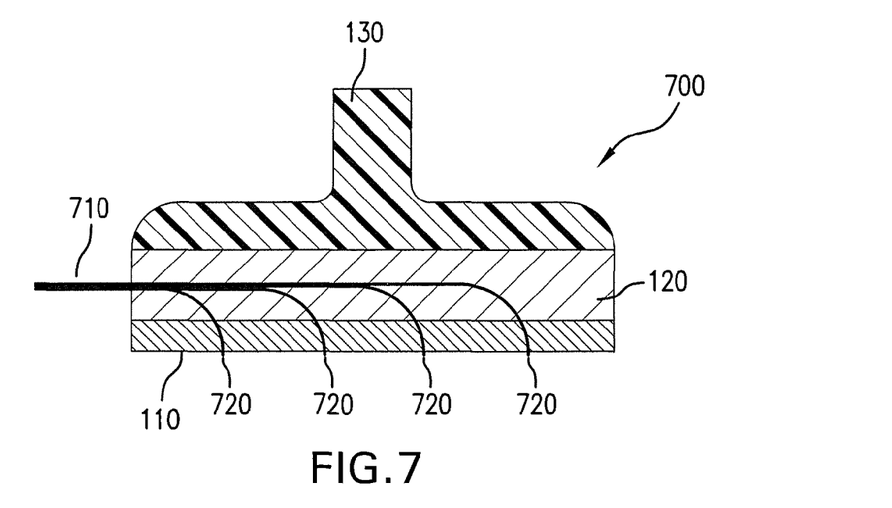
FIG. 7 is a side cross-sectional view of a sixth exemplary apparatus that can be used to produce the hypopigmentation cryogenically in the skin tissue according to an exemplary embodiment of the present disclosure.

Hypopigmentation effects based on contact cooling of the skin surface, as described herein with respect to the various embodiments, can be more effective if a local volume of tissue proximal to the surface is frozen. Cooling of the skin tissue, even when achieved by contacting the skin surface with a plate or other object cooled to below 0 degrees Celsius, e.g., cooled to about −5 to −10 degrees Celsius, may not always lead to local tissue freezing. Such cooling procedures may instead lead to locally supercooled tissue that does not freeze. An exemplary apparatus 700 that can facilitate detection of tissue freezing during the cooling procedure is illustrated in FIG. 7.

The exemplary apparatus 700 can include a cooling arrangement 120 and an optional cooling plate 110 provided on a lower surface of a cooling arrangement 120, and a handle 130. The cooling arrangement 120 can include any cooling device or arrangement described in the various exemplary embodiments herein such as, e.g., those illustrated in FIGS. 1, 2, 4, and 5. For example, the cooling arrangement 120 can include a Peltier device 510 or the like. A handle 130 can be affixed to the cooling arrangement 120 or other portion of the apparatus 700 to facilitate handling and positioning of the apparatus 700. One or more optical conduits 710 can be provided with the apparatus 700, wherein distal ends 720 of the optical conduits 710 can be located proximal to a bottom surface of the cooling plate 110 (or, optionally, a bottom surface of the cooling arrangement 120 if a cooling plate 110 is not provided). The optical conduit 710 can include, e.g., an optical fiber, a waveguide, or the like.

In certain embodiments, the distal end 720 of one or more optical conduits 710 can be provided proximal to the bottom surface of the cooling plate 110, e.g., by locating the distal portion of an optical conduit 710 within a small hole drilled through a portion of the bottom plate 110 or using a similar configuration. Other configurations of the optical conduits 710 can also be provided in further embodiments, where the distal ends 720 of the optical conduits 710 are proximal to the skin surface and/or in optical communication with the skin surface (e.g., there is an unimpeded optical path between the distal end 720 of the optical conduit 710 and the skin surface) when the bottom side of the apparatus 700 is placed against the skin.

To detect freezing of the skin tissue during cooling procedures as described herein, the proximal end of at least one optical conduit 710 can be provided in communication with a source of light or other optical energy (not shown). LEDs or other light sources that emit red light having a wavelength between about 600 nm and about 800 nm can be used. Other wavelengths of light may also be used in further embodiments. For example, light sources that emit light in the near-IR range (e.g., light having a wavelength between about 800 nm and about 2000 nm) may also be used. Such near-IR light may be relatively insensitive to variations in melanin levels of the skin region being treated, and thereby can be used to detect freezing in a variety of skin types.

During the cooling procedure, light can be emitted from the distal end 720 of the at least one optical conduit 710 onto a region of the skin surface beneath the apparatus 700. Light that is reflected and/or scattered by the skin can enter the distal end 720 of at least one optical conduit 710 and directed through the optical conduit 710 to an optical detector (not shown), e.g., a conventional light meter, charge-coupled device (CCD), optical transistor or the like, which can be provided at a proximal end of the optical conduit 710. In further exemplary embodiments, cladding can be removed from other portions of the optical conduit 710 instead of or in addition to at the distal end thereof, to facilitate detection of light directed toward a circumferential portion of the optical conduit 710, thereby facilitating detection of light using other orientations of the optical conduit 710 relative to the skin.

A variation in the intensity or other characteristic of the optical light can indicate the occurrence of local tissue freezing. For example, in certain embodiments the optical conduit 710 used to detect scattered and/or reflected light can be the same as the optical conduit 710 used to direct light onto the skin surface, or positioned very close to the optical conduit 710 used to direct light, e.g., within about 1-2 mm. If tissue freezing occurs, local reflectance of impinging light can increase the amount of light received by the detecting optical conduit 710. Such an increase in an optical signal can be used to confirm freezing of skin tissue when the apparatus 700 is placed on the skin for a particular duration. In further embodiments, the optical conduit 710 can be provided with one or more polarizing elements to reduce or suppress specular reflections from the fiber end and tissue surface, which can provide a more sensitive detection of local tissue freezing.

In further exemplary embodiments, the distal ends 720 of optical conduits 710 used to provide and/or detect light can be spaced further apart, e.g., at a separation distance greater than about 3-4 mm. If tissue freezing occurs, the reflectance of the tissue can increase and more light directed at the skin will be reflected back from the surface region, whereas less light will be scattered laterally through the tissue. Accordingly, a decrease in the detected light signal from such a more distant detecting optical conduit 710 can also indicate local freezing of the skin tissue.

Different configurations of the optical conduits 710 can be provided in further embodiments to detect tissue freezing or to obtain more detail about the tissue freezing as described herein. For example, each of a plurality of the optical conduits 710 can be configured to both direct light onto the skin surface beneath the apparatus and detect light scattered or reflected by the skin tissue. A plurality of such optical conduits 710 (e.g., three or more) can be used to provide information on the depth of freezing of the tissue. Alternatively, a plurality of spaced-apart optical conduits 710 can be configured to either direct light onto the skin or detect light as described herein. The optical detector can be configured and calibrated to detect a threshold change in the optical signal level that indicates freezing proximal to the distal ends of one or more of the optical conduits 710. In certain embodiments, an indicator can be provided, e.g., an LED or light bulb, a sound generator, a digital display, or the like, to confirm the occurrence of tissue freezing while the apparatus 700 is held in contact with the skin surface.

In further exemplary embodiments, temperature sensors 610, e.g., such as those illustrated in FIG. 6, can be configured to detect the occurrence of local tissue freezing. For example, in a typical cooling procedure, the temperature detected by a temperature sensor 610 will correspond to the temperature of the cooling plate 110 that it is in contact with. When the apparatus 600 is placed on the skin surface, the detected temperature will rise as the bottom surface of the cooling plate 110 is warmed slightly by the skin. As conductive cooling of the skin by the plate 110 proceeds, the measured temperature will then decrease. The rate and extent of such decrease can depend on several factors, e.g., the initial temperature, material, and geometry of the plate 110, the efficiency of the cooling arrangement used to cool the plate 110, etc. When tissue freezing occurs proximal to the bottom surface of the cooling plate 110, a slight temporary increase in local temperature may be detected that arises from latent heat released during the freezing phase transformation. The detected temperature may then continue to decrease as further cooling of the frozen tissue proceeds. Accordingly, a "bump" detected in the temporal cooling curve by a temperature sensor 610 can also indicate the occurrence of local tissue freezing.

An exemplary study was performed to illustrate the use of optical sensors to detect the onset of freezing in tissue in accordance with embodiments of the present disclosure. A 20 mm×20 mm flat aluminum contact plate was cooled to a temperature of −7.5 degrees Celsius. Two 1-mm optical fibers were inserted into holes drilled in the plate, with one fiber configured to illuminate the cooled tissue and the second fiber configured to detect light from the tissue as described herein. The cooled plate was placed in contact with a shaved skin surface on the flank region of a female Sinclair pig for 60 seconds. A thermocouple was used to monitor the temperature at a contact point of the cooling plate and the skin surface. The detected light signal was also monitored and recorded during this cooling procedure.

Figure 8:
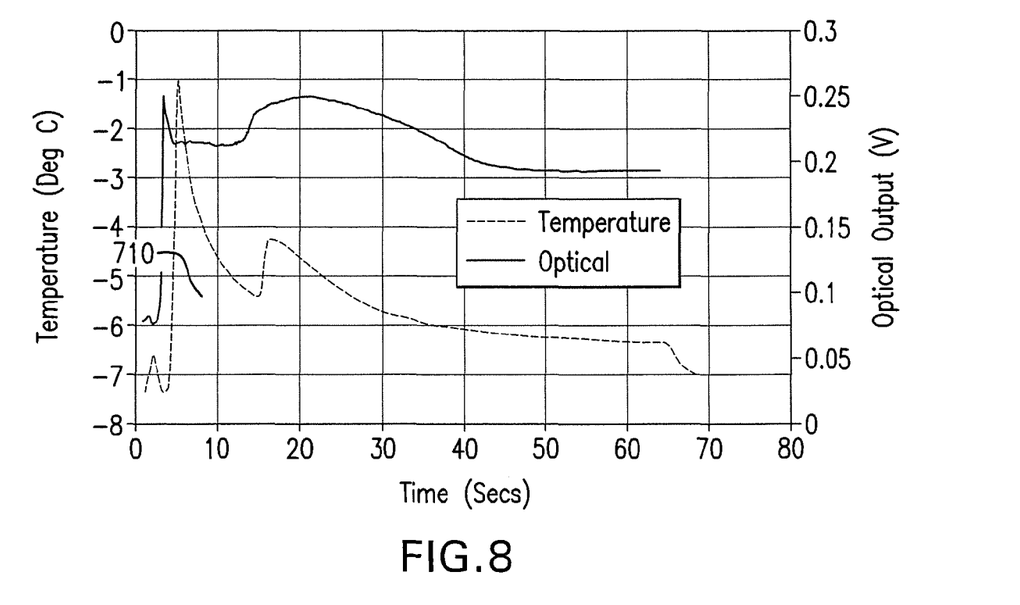
FIG. 8 is an exemplary data plot generated with an apparatus according to an exemplary embodiment of the present disclosure, the plot showing changes in both measured surface temperature and optical reflectance when a region of live pig skin is cooled and local freezing of the skin commences.

An exemplary set of data for this cooling procedure is shown in FIG. 8. The measured temperature (indicated by a dashed line in FIG. 8) was initially observed to rise rapidly (at about 5-6 seconds) when the initially cooled plate was brought into contact with the warmer skin surface. The temperature then dropped as the plate cooled the adjacent skin by thermal conduction. This cooling occurred between about 6 and 15 seconds in the data plot shown in FIG. 8. The optical output (measured in volts using an optical transistor, and indicated by a solid line in FIG. 8) remained fairly constant during this cooling process. At about 15 seconds, a small rise in temperature was detected, indicating the onset of local tissue freezing and release of a latent heat of freezing of the skin. This onset of tissue freezing was accompanied by an increase in the detected optical signal. The optical signal remained elevated as the frozen skin continued to cool. After the cooling plate was removed, it was confirmed that the surface region of the skin was frozen. This study demonstrates the use of optical sensors as described herein to detect the onset of tissue freezing based on a change in detected reflectance level when a skin surface is contacted by a cold object, and the use of temperature sensors to detect the onset of tissue freezing by the presence of a small plateau or transient rise in local temperature associated with a release of latent heat upon freezing.

In still further embodiments, sensors can be provided to facilitate detection of tissue freezing based on measurement of electrical or mechanical impedance. For example, electrical impedance has been shown to change with the onset of freezing in a number of materials including water and tissue. See, e.g., A. A. Gage, Cryobiology 16, pp. 56-62 (1979), B. Rubinsky, Ann. Rev. Biomed. Eng. 02, pp. 157-87 (2000), and T. H. Yu et al., Intl. J. Thermophysics, 24(2) (March 2003). In one embodiment, the electrical impedance can be measured between two or more locations along the bottom surface of the cooling plate 110 that is in contact with the skin surface. Alternatively, separate surface electrodes can be provided proximal to the cooled region and used to measure local electrical impedance of the skin. Such sensors for detecting electrical impedance of the skin can be used with any of the embodiments described herein. Alternatively, a force sensor can be provided to measure local mechanical impedance of the skin tissue. For example, force can be measured locally as a function of tissue displacement with such a force sensor. An accelerometer or some other sensor could also be used to measure a dynamic change in response to a low level impulse or dynamic event. Any of these types of sensors (thermal, optical, mechanical, force, etc.) can be used, either alone or in any combination, in the various embodiments of the invention described herein.

In yet further exemplary embodiments, an indicating arrangement can be provided in communication with any of the sensors and apparatuses described herein that can be used to detect tissue freezing. Such an indicator can include, for example, an indicator light, a buzzer or other sound generator, a display panel, or the like. The indicating arrangement can be configured to provide a first signal to a user to indicate when tissue freezing has been detected. Such a signal can be used to determine the start of the desired treatment time. A timing arrangement 680 (as shown in FIG. 6) can also be provided to indicate the time elapsed since the onset of local tissue freezing has been detected. Optionally, the timing arrangement 670 can be configured to provide a second signal when a predetermined or preprogrammed time interval has passed since the onset of local freezing. This second signal can be used to indicate when the local cooling treatment has ended, and prompt a user to separate the apparatus used from contacting the skin surface. In further embodiments, the timing arrangement 670 may only provide the second signal indicating when the apparatus should be removed from the skin, and not provide the first signal indicating the onset of local freezing.

A heating arrangement can be provided with any of the exemplary apparatuses described herein (see, e.g., a heating arrangement 650 in FIG. 6). The heating arrangement can be used to warm and/or thaw the frozen tissue rapidly after a particular treatment time has elapsed, e.g., it can facilitate more precise control of local tissue freezing duration. Such a heating arrangement can include, e.g., an electrically resistive heating element provided on, within, or proximal to the cold surfaces of any apparatus described herein that is configured to contact and cool the skin. Alternatively, the heating arrangement can include a source of electromagnetic (EM) energy (e.g., a quartz lamp or other infrared emitter, a low-power laser, etc.) configured to direct such EM energy onto the cooled or frozen tissue and warm it by the process of energy absorption. The heating arrangement can also include one or more conduits proximal to the cold surfaces of any apparatus described herein that is configured to circulate a warm fluid and thereby warm the cold surfaces and adjacent cooled tissue. Other conventional heating arrangements can also be used, such as a source of moving warm air (e.g., an arrangement similar to a heat gun or a hair dryer) that can warm the tissue by convection. The heating arrangement can be used while the cooling apparatus is contacting the skin surface, or after the apparatus has been removed from the skin surface, depending on the type of heating arrangement and cooling apparatus used.

Multiple fractional cryotherapy treatments in accordance with any of the exemplary embodiments described herein can be performed on a particular area of the skin to produce further lightening of the skin. Such multiple treatments can be performed at longer intervals, e.g., days or weeks, to allow hypopigmentation effects from a particular treatment to become visually evident before subsequent treatments are performed. Such exemplary multiple treatments can be used to gradually lighten the skin appearance in the treated area. Because the depigmented spots are spatially separated, multiple treatments may be applied to a single area without producing discernible white spots.

In further exemplary embodiments of the present disclosure, a method can be provided for gradually and controllably lightening the appearance of skin tissue by generating hypopigmentation using cryogenic techniques. A region of the epidermal skin tissue can be cooled or frozen to induce hypopigmentation using the exemplary temperatures and times described herein. Portions of the upper dermal layer beneath the frozen epidermal regions can also be frozen or cooled during such exemplary procedures. These exemplary time and temperature exposures can induce a hypopigmentation response in the cooled or frozen skin tissue. Accordingly, the exemplary cryogenic hypopigmentation method(s) described herein can provide a gradual lightening of the area of skin being treated.

The exemplary procedures described herein can be repeated on a particular area of skin to further lighten it. Preferably, the interval between successive procedures can be long enough to allow the hypopigmentation effects to be visibly evident and to better control the overall degree of lightening obtained. Multiple procedures can also be repeated at shorter intervals if desired, for example, to provide a greater overall degree of hypopigmentation in a first area of skin as compared to a second area, using a particular apparatus to provide contact cooling at one or more particular temperatures for one or more particular treatment times.

Various combinations of the cooling arrangements, temperature and/or freezing detectors, and other apparatus features described herein can also be used in further exemplary embodiments of the present disclosure, even where certain combinations may not be explicitly illustrated or described herein in single embodiments. The advantages or characteristics of each of the features can be combined where possible to provide even more advantageous embodiments.

The foregoing merely illustrates the principles of the invention. Other variations to the disclosed embodiments can be understood and effected by those skilled in the art in practising the claimed invention from a study of the drawings, the disclosure, and the appended claims. In the claims, the word "comprising" does not exclude other elements or steps and the indefinite article "a" or "an" does not exclude a plurality. A single processor or other unit may fulfil the functions of several items or steps recited in the claims. The mere fact that certain measures are recited in mutually different dependent claims does not indicate that a combination of these measures cannot be used advantageously. A computer program may be stored/distributed on a suitable medium such as an optical storage medium or a solid-state medium supplied together with or as part of other hardware, but may also be distributed in other forms, such as via the Internet or other wired or wireless telecommunication systems. Any reference signs in the claims should not be construed as limiting the scope of the claims. Various modifications and alterations to the described embodiments will be apparent to those skilled in the art in view of the teachings herein. It will thus be appreciated that those skilled in the art will be able to devise numerous techniques which, although not explicitly described herein, embody the principles of the invention and are thus within the spirit and scope of the invention. All patents and publications cited herein are incorporated herein by reference in their entireties.

What is claimed is:

1. An apparatus for freezing a portion of a skin tissue to lighten a pigmentation appearance of the skin tissue, the apparatus comprising:
    a cooling arrangement;
    a cooling plate having a lower continuous skin contact surface, wherein the lower surface of the cooling plate is configured to contact a surface of the skin tissue to produce a lightened pigmentation of the surface of the skin tissue contacted by the cooling plate;

a thermal control arrangement configured to control the cooling arrangement to cool at least one portion of the cooling plate to a temperature that is between about −5 degrees and −20 degrees Celsius to freeze a basal layer of the skin tissue contacted by the cooling plate to lighten the pigmentation appearance of a portion of the skin tissue, wherein a width of the lower surface of the cooling plate is greater than about 3 cm and less than about 20 cm and is configured for freezing a continuous region of skin to produce the lightening of the surface of the skin tissue;

a sensing arrangement configured to detect an onset of freezing of the basal layer during contact between the lower surface of the cooling plate and the skin tissue; and a timing arrangement configured to monitor an elapsed time following the detection of the onset of the freezing of the basal layer by the sensing arrangement, wherein the timing arrangement is configured to output a signal after elapse of a predetermined treatment time following the detection of the onset of the freezing of the basal layer by the sensing arrangement.

2. The apparatus of claim 1, where in the width of the lower surface of the cooling plate is greater than about 5 cm.

3. The apparatus of claim 1, wherein the cooling plate comprises at least one of a metal or a metal alloy.

4. The apparatus of claim 1, wherein the cooling arrangement comprises at least one of a Peltier device, a reservoir configured to enclose at least one of a refrigerant or a phase change material, or at least one conduit configured to circulate a refrigerant therethrough.

5. The apparatus of claim 1, wherein the cooling arrangement is configured to cool at least one portion of the cooling plate to a temperature that is less than about −7 degrees Celsius.

6. The apparatus of claim 1, wherein the cooling arrangement is configured to cool at least one portion of the cooling plate to a temperature that is between about −7 and −10 degrees Celsius.

7. The apparatus of claim 1, further comprising a temperature sensor.

8. The apparatus of claim 1, further comprising a sensing arrangement configured to detect freezing of the skin tissue proximal to the lower surface of the cooling plate, wherein the sensing arrangement comprises at least one of a temperature sensor or an optical sensor.

9. The apparatus of claim 1, wherein the sensing arrangement comprises at least one optical sensor.

10. The apparatus of claim 9, further comprising an indicating arrangement coupled with the sensing arrangement, the indicating arrangement configured to provide a first signal to a user to indicate when tissue freezing has been detected.

11. The apparatus of claim 10, wherein the first signal is used to determine a start of a desired treatment time.

12. The apparatus of claim 1, further comprising a heating arrangement configured to warm or thaw the tissue after a predetermined treatment time has elapsed.

13. The apparatus of claim 1, wherein the signal indicates when the continuous contact surface should be removed from the skin tissue.

14. A cosmetic method for freezing a portion of a skin tissue to lighten a pigmentation appearance of the skin tissue, the method comprising:

providing a cooling plate;

lightening a pigmentation appearance of the skin tissue by contacting a portion of a surface of the skin tissue with the cooling plate having a continuous skin contact surface to freeze at least a portion of the skin tissue contacted by the cooling plate, wherein a width of the surface of the cooling plate is greater than about 3 cm and less than about 20 cm, and is configured for freezing a continuous region of the skin tissue, and wherein a temperature of the surface of the cooling plate is provided at between about −5 and −20 degrees Celsius to freeze a basal layer of the skin tissue to produce the lightened pigmentation appearance of the surface of the skin tissue; and monitoring an elapsed time following a detection of an onset of the freezing of the basal layer to prevent excessive freezing or tissue damage.

15. The method of claim 14, wherein a temperature of the surface of the cooling plate is provided at between about −7 and −10 degrees Celsius.

16. The method of claim 14, wherein the cooling plate is provided in contact with the skin tissue for a duration that is less than about one minute.

17. The method of claim 14, wherein the detecting of the freezing of the basal layer of the skin tissue is performed proximal to at least a portion of the cooling plate in contact with the skin surface.

18. The method of claim 14, further comprising maintaining the temperature of the cooling plate at a substantially constant temperature while the cooling plate is contacting the portion of the surface of the skin tissue.

19. The method of claim 14, further comprising detecting freezing of the skin tissue.

20. The method of claim 19, wherein the freeze detection is carried out by an optical sensor.

21. The method of claim 14, further comprising rewarming or thawing the frozen tissue after a treatment time.

22. The method of claim 14, further comprising successively placing the cooling plate on the skin surface.

* * * * *